(12) United States Patent
Mitsumoto et al.

(10) Patent No.: US 6,657,079 B1
(45) Date of Patent: Dec. 2, 2003

(54) METHOD FOR MIXING GASES AND APPARATUS THEREFOR

(75) Inventors: Tetsuji Mitsumoto, Himeji (JP); Tatsuaki Yoshimura, Hyogo (JP); Takeshi Nishimura, Himeji (JP); Sei Nakahara, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 42 days.

(21) Appl. No.: 09/640,630

(22) Filed: Aug. 17, 2000

(30) Foreign Application Priority Data

Aug. 23, 1999 (JP) .......................................... 11-235649

(51) Int. Cl.[7] .............................................. C07C 45/34
(52) U.S. Cl. ...................... 562/532; 562/534; 562/535; 568/476; 568/475; 568/470; 366/165.1
(58) Field of Search ................................ 562/532, 534, 562/535; 568/470, 475, 476; 366/165.1

(56) References Cited

U.S. PATENT DOCUMENTS 3,695,192 A * 10/1972 Von Brimer ................. 110/8 A
4,910,008 A * 3/1990 Prudhon ...................... 423/487
5,684,188 A * 11/1997 Hefner et al. ................ 562/532

FOREIGN PATENT DOCUMENTS

GB          2061744 A       5/1981
JP          A-10-244136     9/1998

* cited by examiner

*Primary Examiner*—Deborah D. Carr
(74) *Attorney, Agent, or Firm*—Mathews, Collins, Shepherd & McKay, P.A.

(57) ABSTRACT

A method for mixing a plurality of gases including forming a helical flow within a mixing vessel thereby allowing simplification of construction, avoiding pressure drop to the fullest possible extent, and expediting the mixture lest the volume of a gas within the explosion limits should increase, and an apparatus to be used for the method.

17 Claims, 2 Drawing Sheets

METHOD FOR MIXING GASES AND APPARATUS THEREFOR

BACKGROUND OF THE INVENTION

1. Field of the Invention

This invention relates to a method for mixing a plurality of gases efficiently and an apparatus therefor.

2. Description of the Related Art

As means to mix a plurality of gases, the apparatus described in GB 2061744 A and static mixers are known. They are invariably complicated in construction because they have internal items disposed therein, they give rise to pressure drop during the service, and possibly fail to offer expected services when the gases to be mixed contain an adhesive substance and/or a solid matter.

JP-A-10-244,136 discloses an apparatus which has gas inlet orifices so set that their diameters equal the rates of inflow of the relevant gases to a mixing device. The single mixing device, however, is incapable of adjusting the mixing ratio of the gases being introduced therein.

The method for mixing a plurality of gases is particularly important when the raw materials are mixed for the reaction of catalytic gas phase oxidation. In the reaction of catalytic gas phase oxidation, an organic compound or a gas containing an organic compound is mixed with a gas containing a molecular oxygen. As concrete examples of the reaction of catalytic gas phase oxidation contemplated herein, it may be cited, for example, ethylene oxide from ethylene, maleic anhydride from benzene or $C_4$ hydrocarbon, phthalic anhydride from xylene or naphthalene, acrolein from propylene or propane, acrylic acid from acrolein, methacrolein from isobutylene or tertial butyl alcohol, and methacrylic acid from methcrolein.

FIG. 1 is an explanatory diagram illustrating one example of the conventional gas mixing apparatus. A gas mixing apparatus 1, illustrated in FIG. 1, is a vessel 5 provided, on the lateral face thereof, with a first gas inlet nozzle 2 and a second gas inlet nozzle 3 and in the upper part thereof with a gas outlet 4. This vessel 5 measures 600 mm in diameter and 2850 mm in length (though the length is not easily specified on account of the use of pipes, it is safe to fix the length at the magnitude mentioned above because the required mixture was believed to be completed till the component gases reach the sampling nozzle).

The first gas inlet nozzle 2 measures 550 mm in diameter and the central part of the first gas inlet nozzle 2 is disposed at a position of 550 mm from the bottom of the vessel 5. The second gas inlet nozzle 3 measures 80 mm in diameter and the central part of this second gas inlet nozzle 3 is disposed at a position of 1000 mm from the bottom of the vessel 5. These nozzles are laid as opposed to each other in the direction from the exterior to the interior of the vessel 5.

FIG. 2 is an explanatory diagram illustrating the conventional gas mixing apparatus shown in FIG. 1 as viewed from the gas outlet side (the sampling nozzle is not shown). In the gas mixing apparatus 21 illustrated in FIG. 2, the gases to be mixed are introduced into the vessel 25 via the first gas inlet 22 and the second gas inlet 23, mixed in the vessel 25, and discharged as a mixture via the gas outlet 24.

Generally, the mixing ratio of these gase is decided so as to prevent the mixture from falling within the explosion limits. The substances handled during the course of mixing, depending on their kinds, have an inevitable possibility that they will locally and momentarily form a composition falling in the explosion limits.

For the purpose of mixing gases rapidly as well as simplifyng the construction and avoiding the pressure drop to the fullest possible extent, expediting the mixture lest the gases within the explosion limits should grow in volume, and increasing the yield when the apparatus is used for the production of organic compounds, the mixed gas is required to homogenize at the entry to the reactor for catalytic gas phase oxidation.

SUMMARY OF THE INVENTION

It is an object of this invention to provide a method for mixing a plurality of gases different in kind which incurs pressure drop only in a substantially negligible degree and allows application even to gases containing adhesive substances and/or solid matter, and an apparatus for use in the method.

In mixing a plurality of gases which are capable of forming a composition falling in the explosion limits, the mixed gas of a composition within the explosion limits which is locally formed during the course of mixing is required to reduce in volume by expediting the mixture.

The object of this invention is achieved by a method for mixing a plurality of gases which is characterized by forming a helical flow within a mixing vessel.

The object of this invention is also achieved by an apparatus for mixing a plurality of gases, characterized by having at least one gas inlet nozzle or gas outlet nozzle so disposed as to form a helical flow within a mixing vessel.

According to the apparatus of this invention for mixing gases, since the internal items of the mixing vessel are substantially eliminated or decreased to the fullest possible extent, the gases can be homogeneously mixed with an apparatus exceptionally simple in construction.

According to the method of this invention for mixing gases, the gases can be mixed homogeneously and conveniently.

DESCRIPTION OF THE PREFERRED EMBODIMENTS

Figure 1:
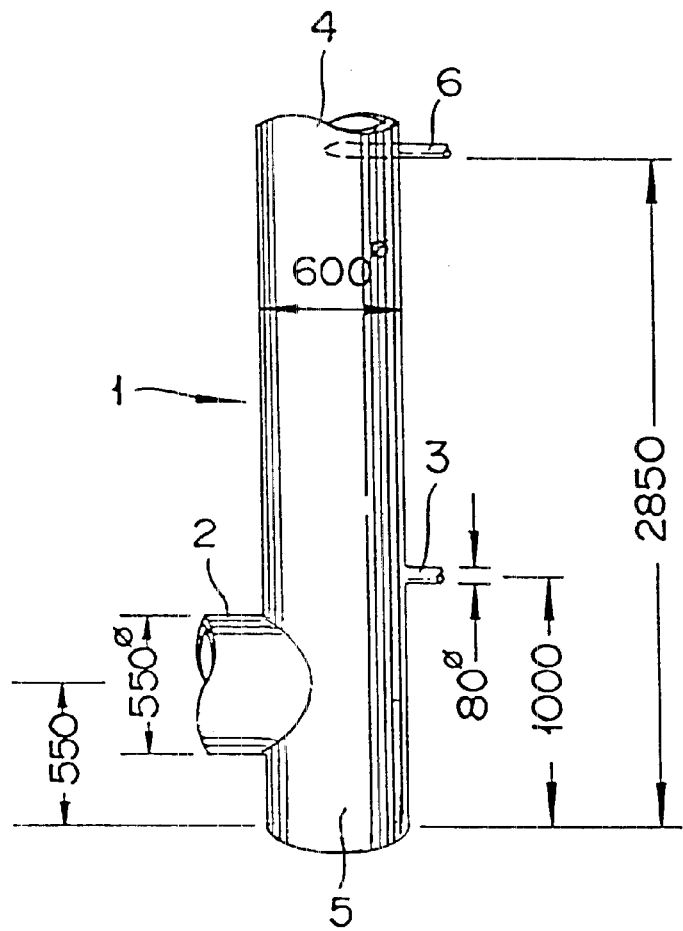
FIG. 1 is an explanatory diagram illustrating a conventional apparatus for mixing gases.
Figure 2:
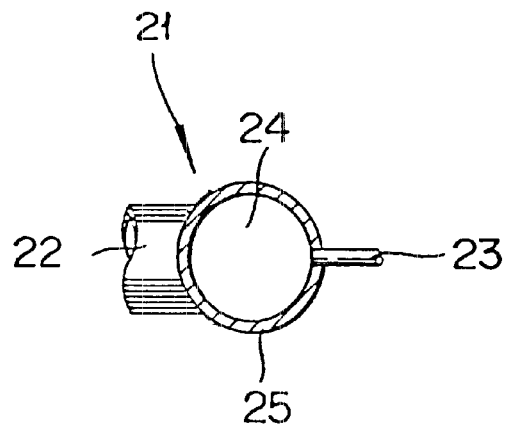
FIG. 2 is an explanatory diagram of the conventional apparatus for mixing gases shown in FIG. 1 as viewed from the gas outlet side.

Now, the method of this invention for mixing a plurality of gases and the apparatus to be used therefor may be explained.

Plurality of gases can be thoroughly mixed by the mixing method characterized by forming a helical flow within a mixing vessel. The formation of a helical flow within the mixing vessel can be accomplished by the apparatus for mixing a plurality of gases which is characterized by being provided with at least one gas inlet nozzle or gas outlet nozzle. The barrel part of the mixing vessel is in a substantially cylindrical shape and is provided at one end thereof with an end plate. The expression "substantially cylindrical shape" as used herein means a conical shape or the combination of a cylindrical shape with a conical shape, and the expression "barrel part of the vessel" refers to the vessel part excluding the end plate. The method for forming a helical flow is not particularly restricted, but cited, for example, methods of projecting nozzles into the interior of a vessel and imparting angles to the projected nozzles; providing the nozzle parts in the vessel with baffles capable of changing direction; connecting nozzles as eccentric to the center of the vessel; and utilizing gas inlet nozzles disposed in tangential directions relative to the barrel part of the vessel. Among other various methods, a method of disposing nozzles in tangential directions relative to the barrel part of the vessel thereby allowing the gases to flow into the vessel through the gas inlet nozzles proves proper from the viewpoint of most simplifying the construction and forming helical flows.

Though the opening parts in the mixing vessel are generally used properly as the outlets for the mixed gas, the method of closing the opening parts with end plates and opening a hole in either of the end plates and using this hole as the gas outlet or the method of closing the opening parts with end plates and forming a gas outlet in the barrel part of the vessel may be adopted. The gas outlet may be fixed in a tangential direction or a perpendicular direction relative to the position of fixing. In short, the gas outlet is preferably disposed so as to avoid obstructing the flow of mixed gas and to fortify the helical flow.

The mixing vessel is preferably operated in a vertical state allowing the opening part of the vessel to serve as the gas outlet from the viewpoint of discharging condensates and/or waste waters of washing after the stop of the apparatus provided with the mixing vessel and restricting the layout of apparatus.

The linear velocity ratios of the gases introduced through the inlet nozzles fall generally in the range of 1.0–4.0 and preferably in the range of 1.0–2.0, based on the latest linear velocity as 1. More preferably, these ratios are specified respectively so as not to include 1.0. If the linear velocity ratios of the introduced gases deviate from the above range, the deviation is at a disadvantage in disrupting the homogeneity of the gases within the vessel and impairing the mixing efficiency.

Further, the retention time of the mixed gas in the vessel interior is properly in the range of 0.3–1.5 second, preferably 0.4–1.0 second. The term "vessel interior" as used herein refers to the barrel part of the mixing vessel and both or either of the end plate parts of the barrel part and does not embrace the volumes of the inlet and outlet nozzles. The end plates at both or either of the opposite ends of the mixing vessel may be any arbitrarily shape such as a normal semi-elliptic, a dished, a hemispheric, or a flat flange shape. Optionally, the end plates may be varied in shape from each other. The retention time is computed based on the total gas flow volumes after the mixing. If the time is less than 0.3 second, it will be insufficient for mixing. If it exceeds 1.5 seconds, the excess will be at a disadvantage in bringing an undue large size to the apparatus and expanding the volume for forming a composition in the explosion limits.

The average linear velocity of the mixed gas inside the vessel is properly in the range of 2.0–10.0 m/sec, preferably 3–7 m/sec in the direction of the gas progress in the cross section of the vessel. The average linear velocity is computed based on the total gas flow volume after the mixing. The term "cross section of the vessel" as used herein means the cross section of the barrel part of the vessel taken in the largest diameter. The restriction of the average linear velocity of the gas to a level of less than 2.0 m/sec requires an increase in the diameter of the barrel part. When the barrel length is secured for thorough mixing of the gases, the retention time is inevitably elongated. If the linear velocity exceeds 10.0 m/second, the excess will be at a disadvantage in increasing the pressure drop.

Since the mixed gas is produced by thoroughly mixing plurality of gases, it is preferably used as the raw material gas for the catalytic gas phase reaction of an organic compound, particularly for the synthesis of (meth)acrolein and/or (meth)acrylic acid. In performing the catalytic gas phase oxidation, it is preferred to introduce at least one member selected from the group consisting of a molecular oxygen-containing gas, steam, and inert gases in advance into the mixing vessel and then introduce an organic compound to the downstream side of the mixed gas lest the gas within the explosion limits including the organic compound should grow in volume.

The method for mixing plurality of gases may be implemented using an apparatus for mixing plurality of gases characterized by having at least one gas inlet or gas outlet nozzle so disposed as to form a helical flow in the mixing vessel.

The inside diameter in the barrel part of the mixing vessel is properly 0.4–1.0 time, preferably 0.5–1.0 time, based on the length of the barrel part in the mixing vessel. When the mixing vessel is in a conical shape or in the combination of a cylindrical shape with a conical shape, the maximum diameter is regarded as the diameter of the barrel part in the vessel. If the diameter is less than 0.4 time based on the length of the barrel part, the shortage will be at a disadvantage in lowering the average linear velocity of the mixed gas progress in the direction of the cross section of the vessel. If the diameter exceeds 1.0 times, the excess will be at a disadvantage in elongating the retention time.

When the gases to be mixed have the possibility of forming a composition falling in the explosion limits, the sequence of gas introduction is important. Each nozzle is preferably disposed so that the distance from the end plate on the upstream side of the mixed gas, namely the end plate on the upstream side of the vessel, to the center of the nozzle in the downstream direction falls in the following position relative to the length of the barrel part of the vessel:

| | |
|---|---|
| Inert gas | 0.05–0.35 |
| Steam | 0.05–0.35 |
| Molecular oxygen-containing gas | 0.05–0.35 |
| Organic compound | 0.40–0.65. |

Here, in the production of acrolein by the catalytic gas phase oxidation of propylene or propane, for example, the organic compound is propylene or propane, the molecular oxygen-containing gas is oxygen gas, and the inert gas is nitrogen gas or carbon dioxide gas. In this case, air may be used as at least part of the mixture of the molecular oxygen-containing gas and the inert gas.

Though these gases may be mixed without any limitation of temperature and pressure, it is preferably carried out at a temperature in the range of 0 to 250° C. and under a pressure in the range of −10 to 150 kPaG.

Now, the gas mixing apparatus and a method for mixing the gases, of the present invention will be described specifically below with reference to the drawings.

Figure 3:
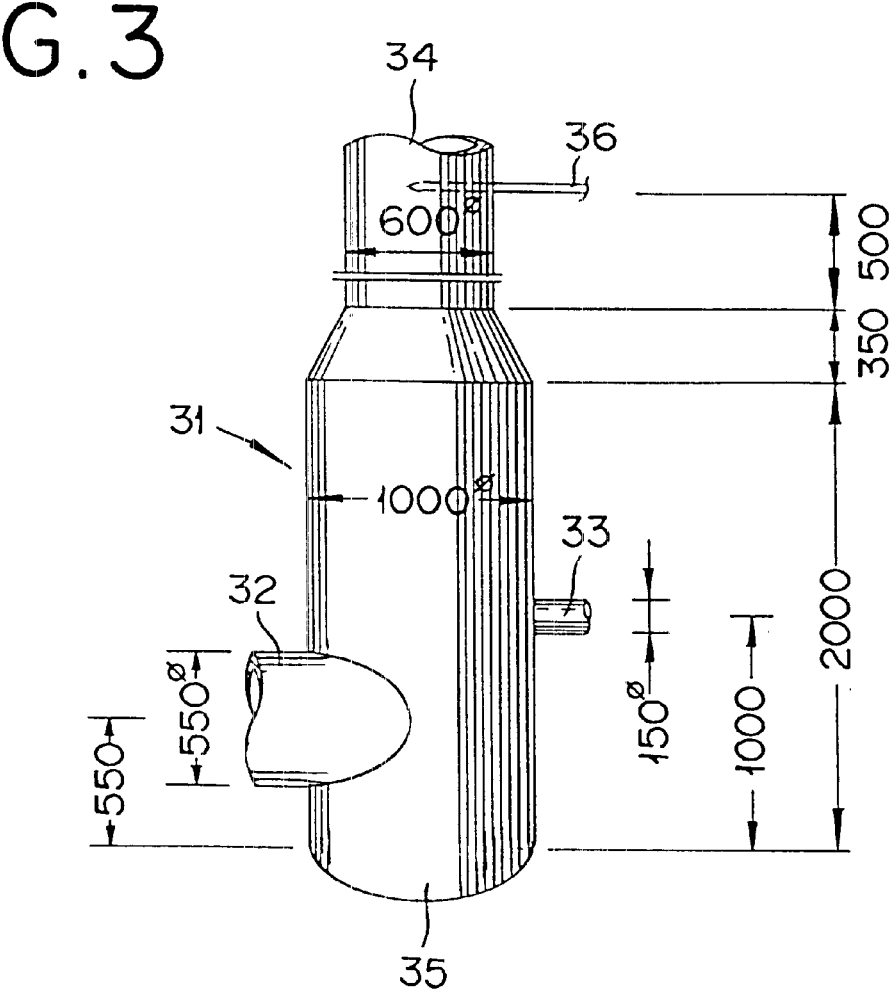
FIG. 3 is an explanatory diagram of an apparatus for mixing gases using a vertical cylindrical vessel which is connected to a pipe as one embodiment of this invention.

FIG. 3 is an explanatory diagram of an apparatus for mixing gases using a vertical cylindrical vessel as one embodiment of this invention. The numerical values of length shown in FIG. 3 are to be interpreted as representing respective ratios and not absolute values unless otherwise specified. As illustrated in FIG. 3, a mixing apparatus 31 is composed of a vessel 35 of substantially cylindrical interior provided in the barrel part thereof with a first gas inlet nozzle 32 and a second gas inlet nozzle 33 and forming a gas outlet 34 in the upper part. The maximum diameter of the barrel part of this vessel 35 is 1000, the diameter of the gas outlet part is 600, the length of the gas outlet part (to the sampling nozzle) is 500, the length of the barrel part is 2350, and the maximum diameter of the barrel part is 0.426 times the length of the barrel part.

The diameter of the first gas inlet nozzle 32 is 550, and the central part thereof is disposed at the position of 550 from the end plate of the vessel 35. Then, the diameter of the second gas inlet nozzle 33 is 150, and the central part thereof is disposed at a position of 1000 from the end plate of the vessel 35. Each nozzle is so disposed as to open generally horizontally from the exterior to the interior of the vessel 35 and in the tangential directions relative to the vessel 35 so that the mixed gas generates a helical flow in one and the same direction. In the introduction of the gases for mixture into the vessel 35, the angle between the first gas inlet nozzle 32 and the second gas inlet nozzle 33 is such that the second gas inlet nozzle 33 is deviated by 180 degrees from the first gas inlet nozzle 32.

The heights of the gas inlet nozzles in this case fall on the downstream side of the mixed gas from the end plate in the lower part of the barrel, specifically 0.234 in the case of the first gas inlet nozzle 32 and 0.426 in the case of the second gas inlet nozzle, relative to the length (2350) of the barrel part of the vessel. Since the first gas inlet nozzle 32 fulfills the relation of 0.05–0.35, it is suitable for the inlet nozzle used for introducing the inert gas, steam, and molecular oxygen-containing gas. Since the second gas inlet nozzle 33 fulfills the relation of 0.40–0.65, it is suitable for the inlet gas used for introducing the organic compound. They may well be rated suitable for use with the mixed gas which has the possibility of forming a gas composition in the explosion limits.

Figure 4:
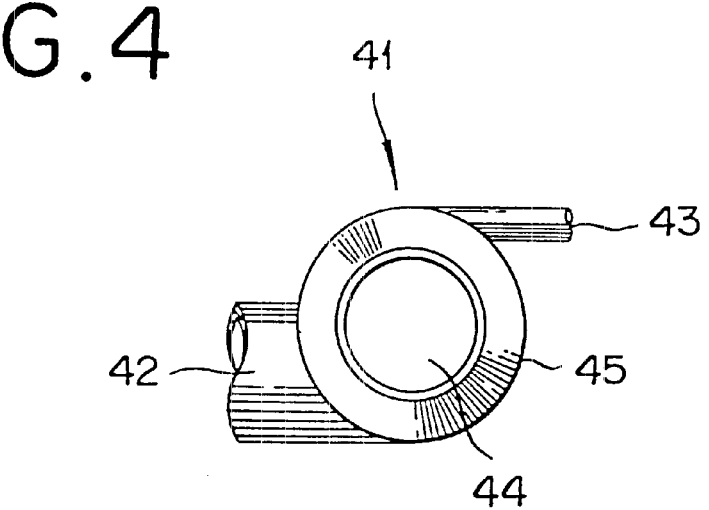
FIG. 4 is an explanatory diagram of the apparatus for mixing gases shown in FIG. 3 as viewed from the gas outlet side.

FIG. 4 is an explanatory diagram of the gas mixing apparatus shown in FIG. 3 as viewed from the gas outlet side. As illustrated in FIG. 4, the gas mixing apparatus 41 introduces the gases to be mixed through the first gas inlet nozzle 42 and the second gas inlet nozzle 43 into the interior of the vessel 45 and discharges the homogeneously mixed gas through the gas outlet 44.

By using the gas mixing apparatus illustrated in FIGS. 3 and 4, it is possible to effect easily the method of mixing the gases.

Though the embodiment of this invention, as described above, has contemplated using a mixing vessel, the mixing method or the mixing apparatus which uses a tubular device instead of a vessel may be implemented. In this case, the length of the vessel constitutes itself the part for substantially performing the mixture of the gases. For example, the region in which the mixture of the plurality of gases by such means as a sampling nozzle is recognized may be interpreted as equaling a mixing vessel.

EXAMPLE

Now, this invention will be described more specifically below with reference to examples, but not restricted by these examples.

EXAMPLE 1

An experiment of mixing gases was carried out using a vertical cylindrical vessel as illustrated in FIG. 3 (materials for parts exposed to gases: stainless steel (SUS 304)), in which the maximum inside diameter of the barrel part of the vessel was 1000 mm and the height of the barrel part of the vessel was 2350 mm.

The inside diameter of the first gas inlet nozzle was 550 mm, the distance from the lower part of the barrel part of the vessel to the center of the nozzle was 550 mm, the inside diameter of the second gas inlet nozzle was 150 mm, and the distance from the lower part of the barrel part of the vessel to the center of the nozzle was 1000 mm, and the first and second gas inlet nozzles were respectively disposed horizontally and in a tangential direction relative to the periphery of the mixing vessel.

The inside diameter of the gas outlet nozzle was 600 mm and the height thereof from the lower part of the barrel part of the vessel was 2350 mm and the nozzles were connected to a gas pipe having the same inside diameter as the that of the gas outlet.

The first gas and the second gas used herein were both air. For the purpose of confirming the mixing ratio of these two gases, the second gas was made to incorporate therein 1.5 vol. % of propylene as a tracer gas.

The linear velocity of the first gas in the inlet nozzle part was 15 m/sec and the linear velocity of the second gas in the inlet nozzle was 18 m/sec. The temperatures of the first gas and the second gas were both 100° C.

At the position of 500 mm from the lower part of the gas outlet nozzle, the mixed gas was sampled at five points in-the radial direction and the samples thus secured were tested for tracer gas concentration. The relative concentration errors at the points of measurement were within ±1% relative to the average concentration of the tracer gas (0.1229 vol. %)

Comparative Example 1

A comparative experiment was performed using an apparatus illustrated in FIG. 1 in place of the vertical cylindrical vessel.

The first and the second gas used herein were both air. For the purpose of confirming the mixing ratio of the two gases, the second gas was made to incorporate therein 1.5 vol. % of propylene as a tracer gas.

The linear velocity of the first gas in the inlet nozzle part was 15 m/sec and the linear velocity of the second gas in the inlet nozzle was 65 m/sec and the temperatures of two gases were both 100° C.

The mixing degree of the gases was determined at a distance of 1850 mm in the downstream direction from the center of the second gas nozzle by the same sampling and analyzing methods as in Example 1. As a result, the relative concentration errors at the point of measurement relative to the average concentration of the trace gas (0.1260 vol. %) were as shown in Table 1. The degrees of mixing were found to give distinct errors.

TABLE 1

|   | (A) | (B) sec. | (C) m/sec. | (D) Cave vol. % | (E) r/R (*1) | (F) C vol. % | (G) (C-Cave) /Cx100 % |
|---|---|---|---|---|---|---|---|
| Example 1 | 1.2 | 0.48 | 4.94 | 0.1229 | 0.8 | 0.1219 | −0.83 |
|   |   |   |   |   | 0.4 | 0.1222 | −0.58 |
|   |   |   |   |   | 0 | 0.1231 | 0.15 |
|   |   |   |   |   | −0.4 | 0.1232 | 0.23 |
|   |   |   |   |   | −0.8 | 0.1241 | 0.98 |

TABLE 1-continued

| | (A) | (B) sec. | (C) m/sec. | (D) Cave vol. % | (E) r/R (*1) | (F) C vol. % | (G) (C-Cave) /Cx100 % |
|---|---|---|---|---|---|---|---|
| Comparative Example 1 | 4.3 | 0.18 (*2) | 13.76 | 0.1260 | 0.8 | 0.0502 | −1144.85 |
| | | | | | 0.4 | 0.1181 | −4.08 |
| | | | | | 0 | 0.1890 | 34.97 |
| | | | | | −0.4 | 0.1123 | −9.45 |
| | | | | | −0.8 | 0.0493 | −149.32 | wherein
- (A): Ratio of linear velocity of introduction
- (B): Retention time in the vessel
- (C): Average rising linear velocity in the vessel
- (D): Average concentration of tracer
- (E): Position of measurement
- (F): Concentration of tracer
- (G): Error of relative concentration (*1) R denotes the radius of the gas outlet pipe, and r denotes the distance from the center of the gas outlet pipe, representing the sampling position.

(*2) The volume of the vessel in Comparative Example 1 was computed as the portions of the lower end plate and the barrel part of the vessel 2350 mm (equaling the height of the vessel in Example 1)

The entire disclosure of Japanese Patent Application No. 11-235649 filed on Aug. 23, 1999 including specification, claims, drawings and summary are incorporated herein by reference in its entirety.

What is claimed is:

1. A method for mixing a plurality of gases, comprising:
   forming a helical flow of at least one member selected from the group consisting of a molecular oxygen-containing gas, stearn, and inert gases in a mixing vessel with at least one gas inlet nozzle; and
   introducing an organic compound to the downstream side of the helical flow for forming a homogeneous mixture prior to performing a reaction of catalytic gas phase oxidation,
   wherein a ratio of linear velocities of the gases to be mixed in the at least one gas inlet nozzle is in the range of 1.0–4.0 based on the lowest velocity as the standard.

2. A method according to claim 1, wherein an average retention time of the mixed gas in the mixing vessel is in the range of 0.3 to 1.5 seconds.

3. A method according to claim 1, wherein an average linear velocity of the mixed gas in the mixing vessel is in the range of 2.0 to 10.0 m/sec.

4. A method according to claim 1, wherein the ratio of linear velocities of the gases is in the range of 1.0–2.0, based on the lowest velocity as the standard.

5. A method according to claim 1, wherein an average retention time of the mixed gas in the mixing vessel is in the range of 0.3 to 1.5 seconds.

6. A method according to claim 5, wherein the average retention time is in the range of 0.4 to 1.0 second.

7. A method according to claim 5, wherein an average linear velocity of the mixed gas in the mixing vessel is in the range of 2.0 to 10.0 m/sec.

8. A method according to claim 7, wherein the average linear velocity is in the range of 3.0 to 7.0 m/sec.

9. A method according to claim 1, wherein an average linear velocity of the mixed gas in the mixing vessel is in the range of 2.0 to 10.0 m/sec.

10. A method according to claim 1, wherein the reaction of catalytic gas phase oxidation is a reaction for the synthesis of (meth)acrolein and/or (meth)acrylic acid.

11. A method according to claim 1, wherein the organic compound is propylene.

12. An apparatus for mixing a plurality of gases comprising having at least one gas inlet nozzle or gas outlet nozzle so disposed as to form a helical flow in a mixing vessel.

13. An apparatus according to claim 12, wherein the mixing vessel is composed of substantially cylindrical vessel.

14. An apparatus according to claim 12, wherein the gas inlet nozzle is disposed horizontally and in a tangential direction relative to the periphery of the mixing vessel.

15. An apparatus according to claim 12, wherein a diameter of the barrel part of the mixing vessel is 0.4 to 1.0 times the length of the barrel part of the vessel.

16. An apparatus according to claim 15, wherein a distance ratio of from the end plate on the upstream side of the mixed gas in the mixing vessel to the center of each nozzle in the downstream direction, based on the length of the barrel part of the vessel, is in the following range:

| | |
|---|---|
| Inert gas | 0.05–0.35 |
| Steam | 0.05–0.35 |
| Molecular oxygen-containing gas | 0.05–0.35 |
| Organic compound | 0.40–0.65. |

17. An apparatus according to claim 12, wherein a distance ratio of from the end plate on the upstream side of the mixed gas in the mixing vessel to the center of each nozzle in the downstream direction, based on the length of the barrel part of the vessel, is in the following range:

| | |
|---|---|
| Inert gas | 0.05–0.35 |
| Steam | 0.05–0.35 |
| Molecular oxygen-containing gas | 0.05–0.35 |
| Organic compound | 0.40–0.65. |

* * * * *